United States Patent
Gururaja et al.

(10) Patent No.: US 7,189,558 B2
(45) Date of Patent: Mar. 13, 2007

(54) **PROCESS FOR PRODUCING PRAVASTATIN SODIUM SALT USING *STREPTOMYCES FLAVIDOVIRENS* DSM 14455**

(75) Inventors: Ramavana Gururaja, Karnataka (IN); Anuj Goel, Karnataka (IN); Madhavan Sridharan, Karnataka (IN); Ramakrishnan Sadhana Melarkode, Karnataka (IN); Madhav Kulkarni, Maharashtra (IN); Acharya Poornaprajna, Karnataka (IN); Deepthy Sathyanathan, Karnataka (IN); Sambasivam Ganesh, Karnataka (IN); Shrikumar Suryanarayan, Karnataka (IN)

(73) Assignee: Biocon Limited, Electronics ( * ) Notice: Subject to any disclaimer, the term of this patent is extended or adjusted under 35 U.S.C. 154(b) by 442 days.

(21) Appl. No.: 10/485,782

(22) PCT Filed: Sep. 27, 2001

(86) PCT No.: PCT/IN01/00161

§ 371 (c)(1),
(2), (4) Date: Feb. 4, 2004

(87) PCT Pub. No.: WO03/027302

PCT Pub. Date: Apr. 3, 2003

(65) Prior Publication Data

US 2004/0209335 A1  Oct. 21, 2004

(51) Int. Cl.
*C12N 1/20* (2006.01)
(52) U.S. Cl. .................. 435/253.5; 435/886; 549/292; 560/179
(58) Field of Classification Search .................. 435/41, 435/253.5; 549/292; 560/179
See application file for complete search history.

(56) References Cited

U.S. PATENT DOCUMENTS

| | | | | |
|---|---|---|---|---|
| 4,448,979 | A * | 5/1984 | Terahara et al. ............ 549/292 |
| 5,179,013 | A * | 1/1993 | Matsuoka et al. .......... 435/125 |
| 6,043,064 | A * | 3/2000 | Davis et al. ................. 435/155 |
| 2004/0253692 | A1* | 12/2004 | Lee et al. .................... 435/135 |
| 2004/0259216 | A1* | 12/2004 | Choi et al. .................. 435/125 |
| 2005/0064566 | A1* | 3/2005 | Lee et al. .................... 435/135 |

* cited by examiner

*Primary Examiner*—Ralph Gitomer
(74) *Attorney, Agent, or Firm*—Andrea L. C. Robidoux; Choate, Hall & Stewart LLP

(57) ABSTRACT

In one aspect, the present invention provides an improved method for the manufacture of Pravastatin sodium salt by fermentation under optimal fermentation parameters using a new strain of *Streptomyces flavidovirens*.

23 Claims, No Drawings

PROCESS FOR PRODUCING PRAVASTATIN SODIUM SALT USING *STREPTOMYCES FLAVIDOVIRENS* DSM 14455

PRIORITY CLAIM

The present application claims the benefit under 35 U.S.C. § 371 of International Application No.: PCT/IN01/00161, filed Sep. 27, 2001, the entire contents of which is hereby incorporated herein by reference.

FIELD OF THE INVENTION

In one aspect, the present invention relates to a process for the manufacture and purification of Pravastatin sodium salt using a new microorganism, *Streptomyces flavidovirens* BICC 6826.

BACKGROUND OF THE INVENTION

Lovastatin, pravastatin, compactin, and derivatives and analogs thereof, are known to be potent HMG-CoA reductase inhibitors and are used as antihyper-cholesterolemic agents. Lovastatin, compactin and pravastatin are produced by fermentation, using microorganisms of different species belonging to *Aspergillus*, *Penicilium* and *Streptomyces* genera, respectively.

The purity of the active ingredient is an important factor for manufacturing a safe and effective pharmaceutical, especially if the pharmaceutical product must be taken on a long-term basis in the treatment or prevention of high plasma cholesterol. Accumulation of impurities from pharmaceuticals of lower purity may cause many side effects during medical treatment of a subject.

Among all the statins produced by microorganisms, pravastatin is has significant advantages in that it exhibits stronger and highly tissue-selective inhibition of cholesterol synthesis (Tsujita et. al, Biochim Biophy Acta, 1986, 877, 50–60). Pravastatin is produced by microbial hydroxylation of its precursor, Compactin (also called ML-236B). This bioconversion is carried out by a number of microorganisms e.g. *Streptomyces* (U.S. Pat. No. 5,179,013, U.S. Pat. No. 4,448,979), *Nocardia, Amycolata, Saccharopolyspora, Amycolatopsis, Saccharothrix, Gilbertella* (EP 0649907, WO 99/60151), *Actinomadura* (WO 96/40863), *Mortierella* (WO 00/46175), *Nocardia* (U.S. Pat. No. 5,830,695) and *Bacillus* sp. (U.S. Pat. No. 6,245,535, WO 99/07827). A number of species of *Streptomyces*, e.g. *S. carbophilus, S. hastedii* (JP 4,349,034), *S. flavovirens* (WO 99/10419), *S. rosenchromogenous* (U.S. Pat. No. 4,346,227), *S. californicus* (EP 649907) and *S. exfoliatus* (WO 98/45410) are also known to carry out this bioconversion.

The bioconversion is a cytochrome p450 dependent system and the enzymes are induced by the presence of compactin in the medium (Matsuoka et al, European Journal of Biochemistry, 1989: 184: 707–713; Serizawa et. al, In: Biotechnology of antibiotics; W R Strohl (editor) 1997). Compactin must often be added into the seed medium for efficient bioconversion (WO 98/45410). Attempts have been made to clone and express this system by recombinant DNA techniques in a fungal host (e.g. *Penicillium citrinum*) for one step de novo production of pravastatin (WO 99/10499). However, the yields are not economically viable. Bioconversion using *Streptomyces* species is still currently the most efficient method of pravastatin production.

SUMMARY OF THE INVENTION

In one aspect, the present invention provides a new strain *Streptomyces flavidovirens* BICC 6826. In another aspect, there is provided a process for efficient conversion and purification of compactin, a compactin salt or a compactin derivative, to pravastatin sodium salt using a new strain of *Streptomyces*.

DETAILED DESCRIPTION OF CERTAIN PREFERRED EMBODIMENTS OF THE INVENTION

In certain embodiments, the present invention provides a process for the manufacture and purification of Pravastatin sodium salt, comprising steps of:

(i) preparing a seed inoculum of a strain of *Streptomyces flavidovirens* capable to 6β-hydroxylating a compound of formula II:

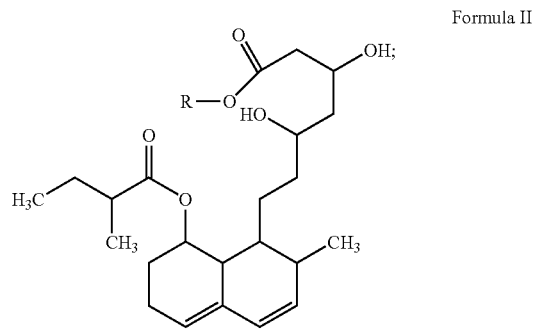

Formula II wherein R is an alkali metal or ammonium ion,
(ii) transferring the seed inoculum to a production medium,
(iii) subjecting the production medium to fermentation,
(iv) feeding a substrate of Formula II in the production medium at different intervals,
(v) controlling the pH during fermentation by feeding a carbon source in the production medium,
(vi) fermenting the substrate until bioconversion to Pravastatin is complete,
(vii) extracting Pravastatin from the whole cell broth, and
(viii) isolating Pravastatin sodium salt of formula I

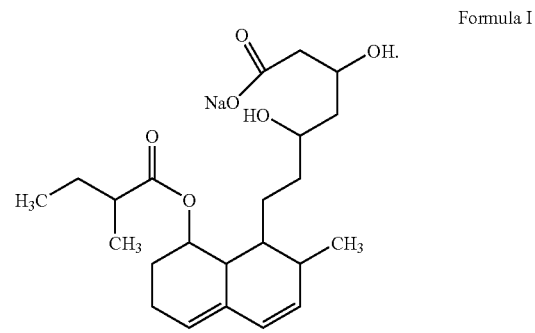

Formula I

In certain embodiments, the strain of *Streptomyces flavidovirens* is *Streptomyces flavidovirens* BICC6826.

In certain other embodiments, the strain of *Streptomyces flavidovirens* is *Streptomyces flavidovirens* strain deposited at DSMZ (Deutsche Sammlung von Mikro-organismen und Zellkulturen GmbH) under accession number DSMZ 14455.

In yet other embodiments, the inoculum used for the seed is a spore suspension or a vegetative mycelium.

In still other embodiments, the seed medium comprises malt extract and peptone.

In certain other embodiments, the pH of the seed medium is between about 6.0 and 7.5 before sterilization.

In yet other embodiments, the seed medium is incubated at between about 25 and 35° C. for about 40 to 55 hours.

In still other embodiments, constituents of the production medium are selected from a group consisting of dextrose monohydrate, peptone and yeast extract.

In certain other embodiments, the production medium has a pH of between about 6.0 and 7.5 before sterilization.

In yet other embodiments, the production medium is incubated between about 24 and 35° C. for about 48 to 148 hours.

In still other embodiments, the substrate used for feeding is compactin, a compactin salt or a compactin derivative.

In certain other embodiments, the pH is controlled by feeding a carbon source selected from a saccharide or glycerol.

In addition to providing a new strain of *Streptomyces flavidovirens* BICC 6826, the present invention has several advantages over the other reported methods, including using a new strain of *Streptomyces flavidovirens* BICC 6826; resuting in a higher bioconversion rate, therefore making the process economically attractive; and involving fewer steps for the isolation and purification process.

*Streptomyces* has been the most commonly used microorganism as its cytochrome system has been well studied (EP 281245, U.S. Pat. No. 5,830,695). Among the *Streptomyces, S. flavidovirens* offers a unique advantage for bioconversion. Unlike *S. exfoilatus* (WO 98/45410) *S. flavidovirens* does not need induction during its vegetative phase. In certain embodiments, bioconversion is between 40 and 90%, preferably between 60 and 80%; with compactin concentrations in the vegetative broth between 0.05 and 10 g/L, preferably between 3 and 6 g/L.

Unlike many cultures reported in the art where the bioconversion is slow and is carried out over 12 days of fermentation (e.g. *Mortierella maculata*, WO 00/46175), *S. flavidovirens* carries out conversion within 24 hrs to 7 days, preferably between 2 to 5 days.

The illustrated embodiments have been set forth only for the purpose of example and should not be taken as limiting the invention. Therefore, it should be understood that within the scope of the appended claims, the invention may be practiced other than specifically described herein.

EXEMPLIFICATION

Example 1

Seed Inoculum Preparation

About 100 µL spore suspension of *Streptomyces flavidovirens* BICC 6826, made by adding 3 mL of sterile water to a culture slant, was added to a 250 mL Erlenmeyer flask containing 35 mL of medium containing 30 g/L malt extract and 5 g/L peptone. pH was adjusted to 6.8 before sterilization. The seed flasks were incubated at 28° C. on a rotary shaker (200-rpm) for 48 hours.

Example 2

Seed Inoculum Preparation

Seed inoculum was prepared in the same way as in Example 1 but the spore suspension was replaced by 1 mL of vegetative mycelium stored in glycerol.

Example 3

Bioconversion to Pravastatin

In 250 mL Erlenmeyer flasks containing 35 mL of production medium containing 20 g/L Dextrose monohydrate, 10 g/L Peptone and 1 g/L yeast extract, was added about 0.5 mL of seed inoculum from Example 2. Before inoculation, the pH of the medium was adjusted to 7.0 and the flasks were sterilized for 30 min at 121° C.

The flasks were then incubated on a rotary shaker (200-rpm) at 28° C. After 2 days of incubation, a sterile solution of compactin sodium salt sodium was added along with sterile dextrose feed (50% w/v). The bioconversion was estimated after 24 hrs by harvesting one of the multiple flasks running under similar conditions. This procedure was repeated every 24 hrs until 3 mg/mL of compactin was fed cumulatively. The maximum amount of pravastatin accumulated at the end of experiment was about 1.5 mg/mL.

Example 4

Bioconversion to Pravastatin

Bioconversion was carried out in 250 mL Erlenmeyer flasks in the same way as described in Bioconversion 3 but 7 mg/mL of dextrose feed was added every 24 hours along with compactin solution. About 2.0 mg/mL of pravastatin was detected in the flasks after 120 hrs of incubation.

Example 5

Bioconversion to Pravastatin

Bioconversion was carried out in a 2L-stirred tank bioreactor with 1.7 L medium. In addition to the medium components described in Example 3, 0.1% (v/v) of silicone antifoam was added before autoclaving the medium.

Seed inoculum (3.5%) was transferred aseptically to the bioreactor and the culture was allowed to grow at 28° C. The dissolved oxygen concentration was maintained above 25% of saturation. After 48 hrs of incubation, about 1 mg/ml of compactin feed was added each day. Dextrose feed was also added along with every compactin feed. The pH of the reaction mixture was maintained between 7.6 to 8.0 by adding dextrose feed as needed. After 4 days, 1.6 g/L of pravastatin was produced.

Example 6

Bioconversion to Pravastatin

Bioconversion was carried out in a similar way as in Example 5, but no sugar was added along with the compactin feed.

About 0.5 mg/ml of compactin feed was added in every compactin addition. The pH of the reaction mixture was maintained between 8.4 and 8.6 by adding dextrose feed as needed. About 46% of the 2.9 g/L of compactin fed to the fermentation vessel was detected as pravastatin.

Example 7

Bioconversion to Pravastatin

Bioconversion was carried out as described in Example 3, but the compactin was added as an ammonium salt. 0.9 g of the total compactin fed (2.9 g/L) was assayed as pravastatin.

Example 8

Extraction of Broth

After fermentation, the whole cell broth was obtained and the pH was adjusted to 12 and held for 1 hr. 90% of the total product present was extracted into the supernatant.

Example 9

Scale up Studies on Hydrophobic Interaction Resin

A hydrophobic interaction resin, SP825, was packed in a XK 26/70 (Pharmacia) column. The pH 12 extracted and filtered broth from Example 8 was passed through a pre-equilibrated column and pravastatin was bound. A washing step was done using pH 12 water. Elution was done with methanol. The overall recovery from the broth extract was 92%.

Example 10

Separation of Pravastatin Using Secondary Amine 80 ml of methanolic extract from the HIC resin containing 10 g pravastatin sodium salt was acidified to pH 4 using dilute HCl and the pravastatin in the acid form was extracted into equal volume of ethyl acetate.

120 Mole % of a dibenzylamine was added to the ethyl acetate extract, and the resulting mixture was stirred for half-hour and then chilled at 4° C. for 1–2 hours. The resulting pravastatin dibenzyamine salt was separated by filtration. The crystals were washed with ethyl acetate, filtered and dried. A pravastatin bibenzylamine salt containing 9 g equivalent of pravastatin acid was obtained.

Example 11

Precipitation of Sodium Salt of Pravastatin Using Sodium Caprylate

Around 5 g of pravastatin amine salt was dried and dissolved in 20 ml of 10% NaOH solution and washed with ethyl acetate. The pH was adjusted to 4 using dilute hydrochloric acid. The resulting mixture was further extracted into equal volume of ethyl acetate.

The ethyl acetate layer was washed with brine, and activated carbon was added and stirred for 30 min at room temperature. The resulting mixture was filtered and washed with ethyl acetate. The ethyl acetate solution was dried over anhydrous sodium sulfate.

To the above ethyl acetate solution was added 1.2 gms of sodium caprylate, and the resulting solution was stirred for 2 hrs at room temperature. 12.5 ml of acetonitrile was added and the resulting solution was stirred for 1 hr. The reaction mixture was cooled to 5° C., and stirred for 1 hr.

The pravastatin sodium salt precipitate was filtered and washed with chilled acetonitrile. The compound was dried under vacuum to give pravastatin sodium in yield of 90% and an assay purity of greater than 99%.

Example 12

Purification of Pravastatin

The broth (10000 L) was acidified to pH=4 by adding 50% ortho phosphoric acid and an equal volume of ethyl acetate was added. The layers were separated and the organic layer was washed with water, concentrated under reduced pressure to give a total volume of about 300 L, and stirred under reflux for 24 h. The solution was cooled to room temperature, washed with 5% sodium bicarbonate solution, followed by water, and concentrated under reduced pressure to 125 L. The residue was chilled to 0° C. and stirred for 2 h. The solid obtained was filtered to give the lactone.

To 1 Kg of the lactone obtained from the above step, methanol (1 L) and 10% sodium hydroxide (2 L) were added and the resulting mixture was stirred for 0.5 h at room temperature. Water (1 L) and ethyl acetate (2 L) were added and the contents were stirred for 10 min at room temperature. The ethyl acetate layer was separated and discarded. The pH of the aqueous layer was carefully adjusted to 4 using 6N HCl and was extracted with ethyl acetate (4 L). The layers were separated, and the ethyl acetate layer washed with brine. Activated charcoal was added. The resulting mixture was filtered and the filtrate was dried over sodium sulfate. After filtration, sodium caprylate (347 g) was added to the filtrate and the contents were stirred for 1 h, after which time acetonitrile (2.5 L) was added. Stirring was continued for additional 2 h, the solution was chilled to 0° C., and the solid pravastatin sodium salt that precipitated was filtered and dried at 40° C. under vacuum.

The crude sodium salt was dissolved in 2 L of water and acetonitrile was added (30 L) over a period of 2 h. The contents were chilled to 0° C. and were stirred for 4 h at 0° C. The resulting solid was filtered and is washed with acetonitrile. The solid was dried under vacuum at 40° C. to give pharmaceutical grade pravastatin sodium salt.

Example 13

Purification of Pravastatin

To the ethyl acetate layer obtained in Example 12, sodium acetate was added instead of sodium caprylate, and the resulting mixture was processed to give pharmaceutical grade pravastatin sodium salt.

Example 14

Purification of Pravastatin 100 gm crude pravastatin lactone, obtained in a similar way as in Example 12 was added to 300 ml alkaline methanolic solution. The pH of the solution was adjusted to 4 and the pravastatin acid was extracted into 400 ml Ethyl acetate. 120 Mole % dibenzylamine was added to the ethyl acetate solution. The resulting solution was stirred for 1 hour, chilled at 4° C. and filtered. The crystals were dissolved in methanol, the pH was adjusted to 4 by addition of dilute hydrochloric acid and pravastatin was extracted into ethyl acetate. To the ethyl acetate solution was added 90 mole % sodium caprylate, and the resulting mixture was stirred well. Crystals of the sodium salt precipitated out when acetonitrile was added to the solution, which was chilled for 1 hour. The product was obtained in 70% yield with greater than 99% assay purity.

We claim:

1. A strain of *Strepomyces flavidovirens* deposited at Deutsche Sammlung von Mikro-organismen und Zelikulturen GmbH under accession number DSM 14455.

2. A microbial process for preparing a compound of formula I

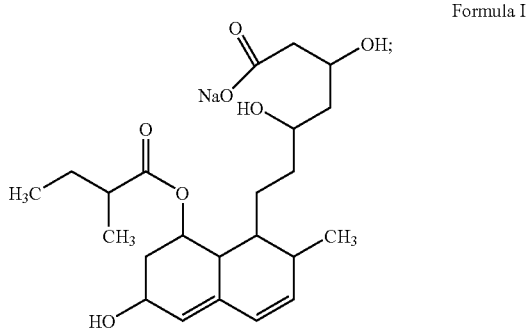

Formula I from a substrate compound of general formula II,

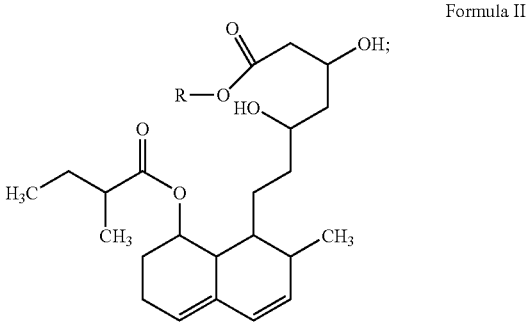

Formula II wherein R represents an alkali metal or ammonium ion, comprising steps of
   (i) preparing a seed inoculum of a strain of *Streptomyces flavidovirens* that 6β-hydroxylates a compound of formula II,
   (ii) transferring the seed inoculum to a production medium,
   (iii) subjecting the production medium to fermentation,
   (iv) feeding a substrate of Formula II in the production medium at different intervals,
   (v) controlling the pH during fermentation by feeding a carbon source in the production medium,
   (vi) fermenting the substrate until bioconversion to Pravastatin is complete,
   (vii) extracting Pravastatin from the production medium, and
   (viii) isolating Pravastatin sodium salt.

3. The process of claim 2, wherein the strain of *Streptomyces flavidovirens* is the *Strepbomyces flavidovirens* strain deposited with DSMZ (Deutsche Sammlung von Mikroorganismen und Zellkulturen GmbH) under accession number DSMZ 14455.

4. The process of claim 2 wherein the inoculum used for the seed is a spore suspension or a vegetative mycelium.

5. The process of claim 2 wherein the substrate is compactin, a compactin salt or a compactin derivative.

6. The process of claim 2 wherein the seed inoculum comprises malt extract and peptone.

7. The process of claim 2 further comprising a step of incubating the seed inoculum.

8. The process of claim 7 wherein the seed medium is incubated between about 25 and 35° C. for about 40 to 55 hours.

9. The process of claim 2 wherein constituents of the production medium are selected from the group consisting of dextrose monohydrate, peptone and yeast extract.

10. The process of claim 2 further comprising a step of incubating the production medium.

11. The process of claim 10 wherein the production medium is incubated between about 24 and 35° C. for about 48 to 148 hours.

12. The process of claim 2 wherein the carbon source is selected from a saccharide or glycerol.

13. The process of claim 12 wherein the carbon source is dextrose.

14. The process of claim 2 wherein the step of isolating Pravastatin sodium salt comprises converting Pravastatin isolated from the cell broth to its dibenzylamide salt.

15. The process of claim 14 wherein the dibenzylamide salt is converted to Pravastatin sodium salt by reaction with sodium caprylate.

16. The process of claim 2 wherein in the step of extracting Pravastatin from the whole cell broth, Pravastatin is obtained in its lactone form.

17. The process of claim 2 wherein in the step of extracting Pravastatin from the whole cell broth, Pravastatin is obtained as its lactone form, and the step of isolating Pravastatin sodium salt comprises converting the lactone to Pravastatin acid.

18. The process of claim 17 wherein converting the lactone to Pravastatin acid comprises contacting the lactone with a methanolic solution of sodium hydroxide.

19. The process of claim 17 wherein Pravastatin acid is further converted to Pravastatin sodium salt by reaction with sodium caprylate.

20. The process of claim 17 wherein Pravastatin acid is further converted to Pravastatin sodium salt by reaction with sodium acetate.

21. The process of claim 17 wherein Pravastatin acid is further converted to Pravastatin dibenzylamide salt by reaction with dibenzylamine.

22. The process of claim 21 wherein Pravastatin dibenzylamide salt is further converted to Pravastatin sodium salt by reaction with sodium caprylate.

23. A composition comprising a strain *Streptomyces flavidovirens* DSM 14455 and compactin, a compactin salt or a compactin derivative.

* * * * *